(12) United States Patent
Forest et al.

(10) Patent No.: US 11,986,528 B2
(45) Date of Patent: May 21, 2024

(54) USE OF A MIXTURE OF LAUROYL MACROGOLGLYCERIDE AND POLYETHYLENE GLYCOL AS AN EXCIPIENT

(71) Applicant: GATTEFOSSE SAS, Saint-Priest (FR)

(72) Inventors: Amandine Forest, Lyons (FR); Jean-David Rodier, Villeurbanne (FR)

(73) Assignee: GATTEFOSSE SAS, Saint-Priest (FR)

( * ) Notice: Subject to any disclaimer, the term of this patent is extended or adjusted under 35 U.S.C. 154(b) by 52 days.

(21) Appl. No.: 17/443,485

(22) Filed: Jul. 27, 2021

(65) Prior Publication Data
US 2022/0040311 A1 Feb. 10, 2022

(30) Foreign Application Priority Data
Aug. 5, 2020 (FR) ...................................... 2008312

(51) Int. Cl.
*A61K 47/36* (2006.01)
*A61K 9/16* (2006.01)
*A61K 47/10* (2017.01)

(52) U.S. Cl.
CPC ............ *A61K 47/36* (2013.01); *A61K 9/1682* (2013.01); *A61K 47/10* (2013.01)

(58) Field of Classification Search
CPC ...... A61K 47/36; A61K 9/1682; A61K 47/10; A61K 2800/41; A61K 8/0241; A61K 2800/10; A61K 2800/5922; A61K 2800/594; A61K 8/86; A61K 47/14; A61K 47/34; A61K 9/1647; A61K 8/0216; A61K 8/85; A61K 9/1641; A61Q 19/00
See application file for complete search history.

(56) References Cited

U.S. PATENT DOCUMENTS

2003/0220391 A1 11/2003 Bogardus et al.
2016/0120964 A1* 5/2016 Shlieout ............... A61P 1/00
424/94.21

FOREIGN PATENT DOCUMENTS

EP 1972336 A1 9/2008

OTHER PUBLICATIONS

Sutananta et al. International Journal of Pharmaceutics 111, (1994) 51-62 (Year: 1994).*
Serajuddin et al. Journal of Pharmaceutical Sciences vol. 77, No. 5, 1988 (Year: 1988).*
Chambin, O., Jannin, V. Drug Development and Industrial Pharmacy 31:527-534, 2005 (Year: 2005).*
Madhav, Vasanthavada et al., "Lipid-Based Self-Emulsifying Solid Dispersions" Bull. Korean Chem. Soc., Nov. 6, 2007, Wiley—V C H Verlag GmbH & Co. KGaA, DE, XP55797152, vol. 38, pp. 149-183.

* cited by examiner

*Primary Examiner* — Susanna Moore
*Assistant Examiner* — Luisalberto Gonzalez
(74) *Attorney, Agent, or Firm* — Heslin Rothenberg Farley & Mesiti P.C.

(57) ABSTRACT

The invention concerns the use, as a pharmaceutical or cosmetic excipient, of a composition which is solid at ambient temperature and in the form of individualized particles, said composition comprising:
  lauroyl macrogolglyceride,
  polyethylene glycol.

9 Claims, 5 Drawing Sheets

[Fig. 1]
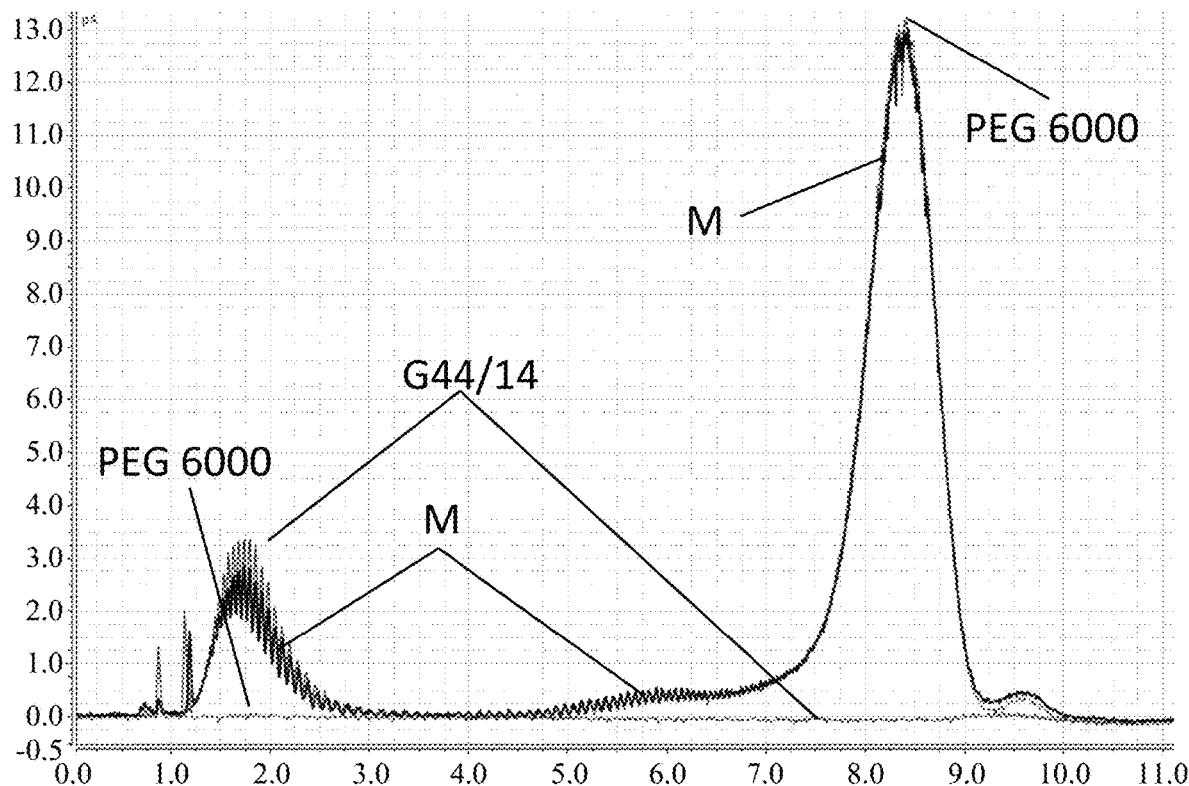
[Fig. 2]

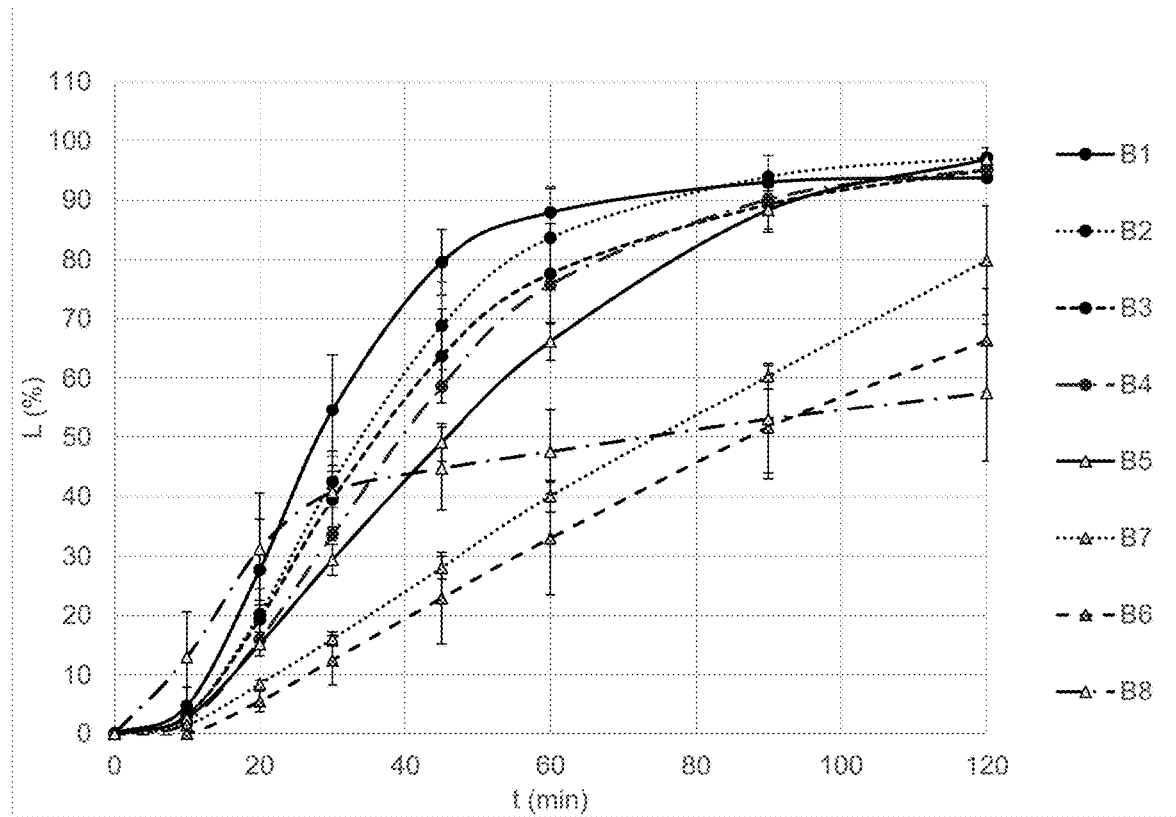
[Fig. 3a]

[Fig. 3b]
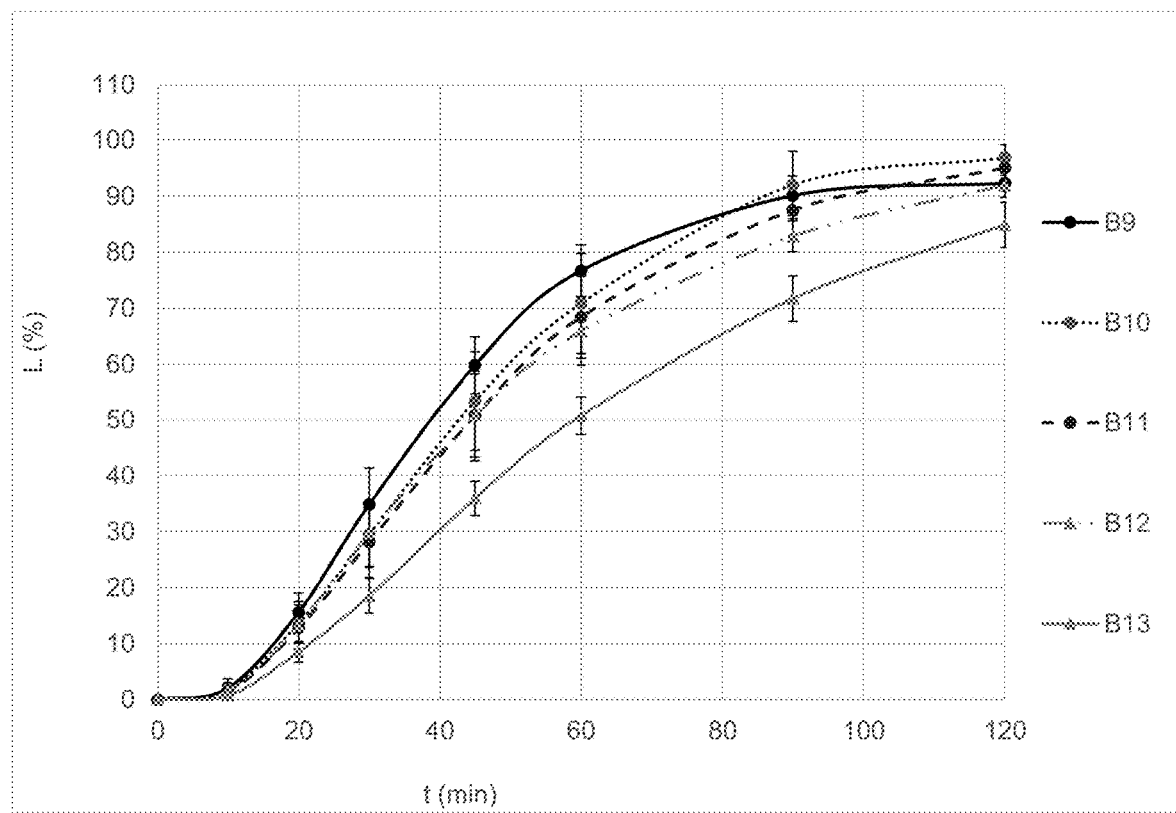

[Fig. 4]
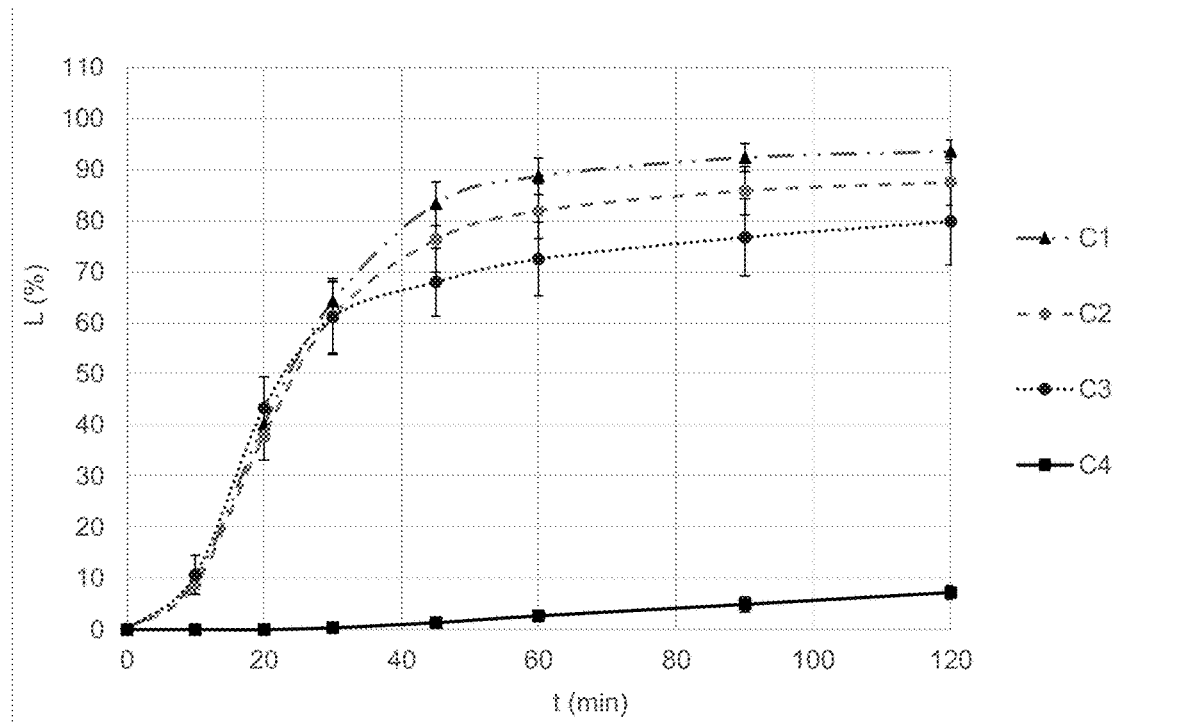

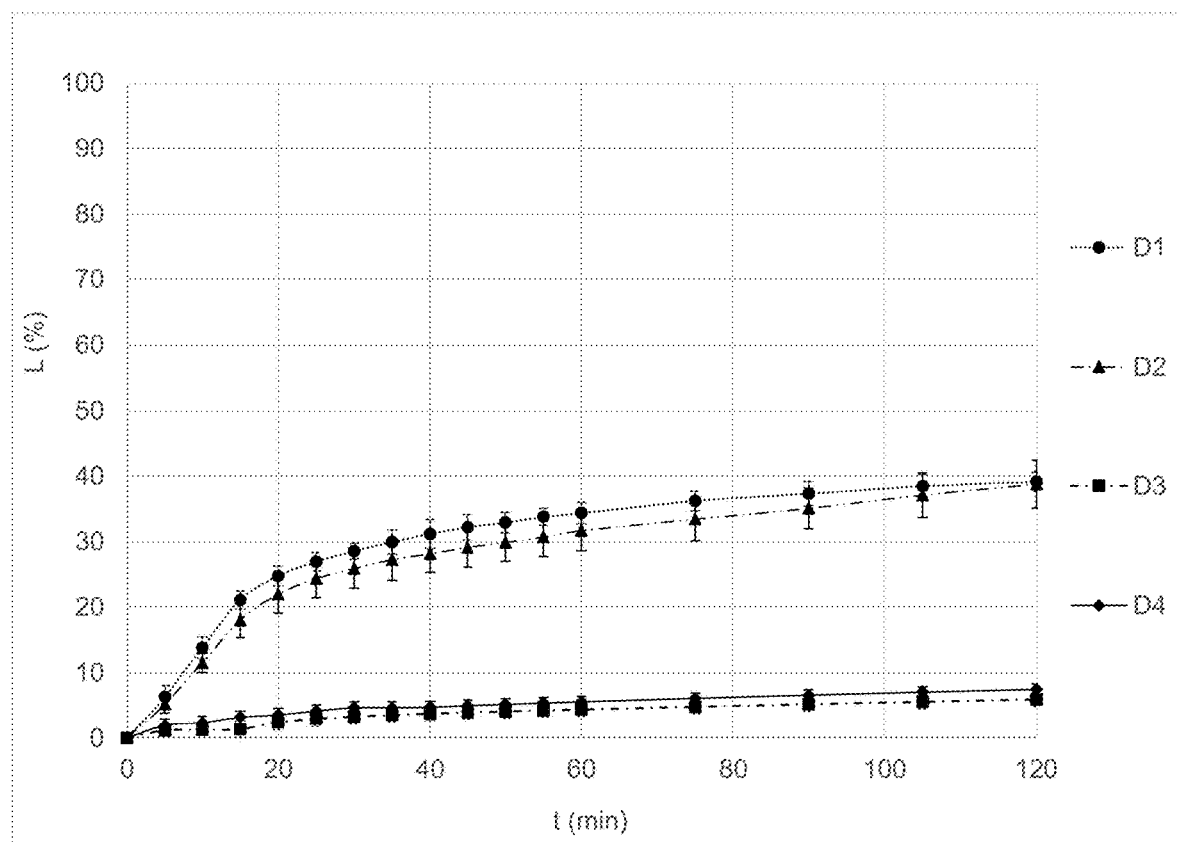
[Fig. 5]

USE OF A MIXTURE OF LAUROYL MACROGOLGLYCERIDE AND POLYETHYLENE GLYCOL AS AN EXCIPIENT

This application claims priority to French application number 2008312 filed on Aug. 5, 2020, the entire contents of which are hereby incorporated herein by reference.

The present invention relates to an excipient for pharmaceutical or cosmetic use, based on lauroyl macrogolglyceride and polyethylene glycol (PEG or macrogol). It also concerns a method for the production of a pharmaceutical or cosmetic composition comprising an excipient of this type.

Gelucire® 44/14, identified in the European Pharmacopeia by the name "Lauroyl Macrogolglyceride", is a known excipient which has been marketed by the Applicant for a number of years. This product is constituted by a mixture of glycerol mono-, di- and triesters and mono- and diesters of PEG with saturated fatty acids containing 8 to 18 carbon atoms. The mixture also contains a small proportion of PEG and free glycerol. Mixtures of this type may be obtained by a reaction for the alcoholysis of a hydrogenated vegetable oil, for example hydrogenated coprah oil, using polyethylene glycol. This oil is in turn constituted by triglycerides containing the fatty acids described above. An excipient of this type may also be obtained by the esterification of glycerol and PEG with the fatty acids described above, or in fact by a mixture of esters of glycerol and a condensate of ethylene oxide with said fatty acids. Gelucire® 44/14 has a melting point of approximately 44° C. and an HLB of 14.

As mentioned above, Gelucire® 44/14 is widely used as an excipient in pharmaceutical compositions or even sometimes in cosmetic compositions, in particular because of its properties of improving the solubility of active principles in particular, and their bioavailability.

In this regard, the document EP 1 972 336 describes a process for the production of micro-pellets with a diameter which is of the order of one micrometer, in particular less than 500 micrometers. These micro-pellets comprise ketoprofen dispersed in a matrix of Gelucire® 44/14 or PEG 4000 or Lutrol F68, each of the excipients being demonstrated to be capable of dissolving an active principle.

The document US 2016/120964 describes pharmaceutical compositions obtained by wet granulation constituted by porcine pancreatin which is used as the active principle, and also Gelucire® 44/14 and PEG 4000.

The document US 2003/220391 describes capsules containing a derivative of taxane, and also Gelucire® 44/14 and PEG 1450. In practice, the Gelucire® 44/14 and the PEG are introduced separately into a heated vessel. Once the mixture is in the liquid state, the active principle is introduced into the vessel and finally, the capsules are filled with the mixture obtained.

Gelucire® 44/14 is a pasty product which is offered in the form of a heterogeneous block. It cannot be packaged in a divided form, i.e., for example in the form of granules, pellets or flakes.

Handling Gelucire® 44/14 in fact necessitates melting the entire sample before using it, even if the quantity desired for the formulation is smaller than the quantity of the sample. This operation is necessary in order to ensure that the quantity which is removed is homogeneous. It necessitates using an oven, and therefore involves the manipulation of a hot liquid product, which constitutes a first disadvantage. Furthermore, the manipulation of the material could result in losses which depend on the final quantity which is used: this constitutes a second disadvantage.

Thus, Gelucire® 44/14 is a product which necessitates specific handling as well as precision as regards the quantity to be used, and this is in need of improvement.

The document XP 55797152 separately describes the use of Gelucire® 44/14 and PEG as a pharmaceutical excipient in order to improve the solubility and bioavailability of pharmaceutical active principles.

Thus, one aim of the invention is to make the manipulation of Gelucire® 44/14 during the preparation of pharmaceutical or cosmetic formulations easier and more rapid.

Another aim of the invention is to make it possible to pick up quantities of Gelucire® 44/14 which are smaller than that contained in an industrial wrap, while ensuring that the quantity which is picked up is homogeneous.

The Applicant has established that, completely surprisingly, manipulation by the formulator of Gelucire® 44/14 at ambient temperature is facilitated when it is combined with PEG. This PEG has the feature of being solid at ambient temperature. In fact, it has been shown that it is possible to obtain a divisible solid form of Gelucire® 44/14. The formulator therefore has Gelucire® 44/14 available in the solid individualized form which can be used in exactly the desired quantity.

In other words, the invention concerns the use, as an excipient in a pharmaceutical or cosmetic formulation, of a composition which is solid at ambient temperature, in the form of individualized particles, said composition comprising:

lauroyl macrogolglyceride (which is the equivalent chemical name for the trade name Gelucire® 44/14),
polyethylene glycol.

As a consequence, because it is being used as an excipient, the solid composition of the invention does not contain any therapeutic active principle. Accordingly, the composition does not comprise a therapeutically active ingredient (e.g., an active pharmaceutical ingredient (API), which is the biologically active component of a drug product).

In some embodiments, the lauroyl macrogolglyceride and the polyethylene glycol constitute 90 to 100 wt % of the composition based on the total weight of the composition (e.g., 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100 wt %), including any and all ranges and subranges therein (e.g., 95-100 wt %, 99-100 wt %, etc.).

In some embodiments, with the exception of lauroyl macrogolglyceride, polyethylene glycol, and optionally color additives, the composition does not comprise more than 5 wt % of any other single ingredient based on the total weight of the composition. For example, in some embodiments, the composition does not comprise more than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 wt % of any other single ingredient.

The mixture of lauroyl macrogolglyceride with a polyethylene glycol does not involve a chemical reaction. No new chemical entities are created when mixing Gelucire® 44/14 with PEG: this has been experimentally verified.

FIG. 1 is a graph which can be used to compare a Gelucire® 44/14/PEG 6000 mixture in a ratio by weight of 65/35 with the distribution of PEG 6000 and Gelucire® 44/14 in isolation. These results were obtained using HPLC-CAD (Charged Aerosol Detector). In FIG. 1, the Gelucire® 44/14 is denoted as G44/14, and the Gelucire® 44/14/PEG 6000 mixture is denoted as M. It can be seen that no chemical entities other than the Gelucire® 44/14 and the PEG 6000 are present on this graph, thereby confirming the absence of reaction between the PEG and the Gelucire®.

As already mentioned, Gelucire® 44/14 contains saturated C8 to C18 mono-, di- and triglycerides and mono- and diesters of PEG 1500 with C8 to C18 fatty acids. It may optionally contain free glycerol and free PEG 1500. Nevertheless, it is clear that the PEG mentioned in the paragraph above is added to the Gelucire® 44/14, i.e. optionally to the fraction of PEG initially present in the Gelucire® 44/14. In other words, the PEG does not originate from free PEG 1500 present in the Gelucire® 44/14.

In an advantageous embodiment, the composition contains only these two constituents, Gelucire® 44/14 and PEG, and is solid at ambient temperature.

The Applicant has established that particularly advantageous results are obtained when the molar mass of PEG is in the range 1500 g/mol to 8000 g/mol, advantageously in the range 4000 g/mol to 6000 g/mol.

Advantageously, the Gelucire® 44/14/polyethylene glycol weight ratio is in the range 40/60 to 70/30.

Polyethylene glycol (PEG) is an excipient with a high melting point, in the range from approximately 53° C. to approximately 59° C. for PEG 4000, and in the range from approximately 55° C. to 62° C. for PEG 8000. The addition of this PEG to Gelucire® 44/14 means that a solid and non-pasty mixture can be obtained. In contrast to Gelucire® 44/14 alone, the mixture of Gelucire® 44/14 and PEG can therefore be divided, i.e., it is possible to produce individualized particles such as pellets, rather than forming blocks of Gelucire®.

The composition may comprise a single PEG or a mixture of at least two different PEGs, i.e. with different molar masses, in identical or different quantities. In the case of a mixture of PEGs, more advantageously, the PEGs all have a molar mass in the range 1500 g/mol to 8000 g/mol, and preferably in the range 4000 g/mol to 6000 g/mol.

The molar mass of PEG and the Gelucire® 44/14/polyethylene glycol weight ratio which have been described are relative to the PEG which is added to the Gelucire® 44/14 initially containing a fraction of PEG 1500.

When the solid composition comprises several different PEGs, the weight ratio described above is calculated with respect to the total mass of the PEGs. As an example, when the solid pellet comprises two different PEGs, denoted PEG 1 and PEG 2, the weight ratio is as follows: weight of Gelucire® 44/14/(weight of PEG 1+weight of PEG 2). This ratio is in the range 40/60 to 70/30.

In practice, the individualized particles have a dimension of at least 1 mm. The expression "individualized particles" means particles, preferably pellets, with a dimension which is in the range 1 mm to 15 mm, and advantageously in the range mm to 10 mm.

The Applicant has established that it is possible to obtain pellets which are not sticky and are whole, in particular in the ranges of molar masses and weight ratios defined above.

Pellets of this type are obtained by a pelletization step which is well known to the person skilled in the art. This pelletization may be carried out manually with the aid of a pipette, or on an industrial scale with the aid of an industrial pelletizer.

A pellet is an article with a substantially flat face and a curved face. The characteristic dimension of the solid pellet is preferably 1 mm or more, and advantageously, and preferably, 5 mm or more. The characteristic dimension corresponds to the greatest length of the flat face of the pellet. When the pellet is substantially round, in the form of a disk, the characteristic dimension corresponds to the diameter of the flat face. When the flat face of the pellet is oblong in shape (an ellipse), the characteristic dimension corresponds to the maximum diameter of the flat plate, i.e. the major axis of the ellipse.

In pellet form, the mixture of Gelucire® 44/14 and PEG can easily be manipulated by the industrial formulator, and in complete safety, in contrast to Gelucire® 44/14 alone in the form of a pasty block which has to be melted in its entirety. The industrial formulator can easily weigh and manipulate the quantity of pellets necessary for the preparation of the active mixture without the need for melting the entirety of the block of Gelucire® 44/14 and handling a liquid at a high temperature.

The Applicant has demonstrated that the use, in combination with Gelucire® 44/14, of a PEG with a molar mass which is advantageously in the range 1500 g/mol to 8000 g/mol, more preferably in the range 4000 g/mol to 6000 g/mol, and with a Gelucire® 44/14/polyethylene glycol weight ratio which is advantageously in the range 40/60 to 70/30, improves the dissolution properties the active principle alone.

In accordance with the invention, the method for the production of the composition comprises the following steps:
  heating the Gelucire® 44/14 and polyethylene glycol (PEG) to a temperature T1 in a manner such as to obtain a liquid mixture of Gelucire® 44/14 and polyethylene glycol,
  cooling the mixture of lauroyl macrogolglyceride and polyethylene glycol to a temperature T2 which is lower than the temperature T1, while keeping the mixture liquid,
  dividing the cooled mixture, advantageously into the form of drops and droplets,
  cooling the divided mixture, advantageously in the form of drops and droplets, to a temperature T3 which is lower than the temperature T2 in order to obtain the individualized solid particles.

The temperature T3 is advantageously ambient temperature, in the range 20° C. to 25° C.

Preferably, before the cooling step, the mixture of Gelucire® 44/14 and PEG is stirred for at least 15 minutes at the temperature T1.

The Gelucire® 44/14 and the PEG are preferably mixed with each other before the heating step, then the mixture of Gelucire® 44/14 and polyethylene glycol is heated to the temperature T1.

Advantageously, a temperature T1 of greater than or equal to 80° C. is selected in order to ensure that the entirety of the Gelucire® 44/14 and PEG has melted and is in the liquid state.

Furthermore, advantageously, a temperature T2 of 45° C. or higher is selected, preferably 55° C. or higher, and less than or equal to 60° C., so that the cooling is relatively gentle and that the quantity of heat to be evacuated is not too great, in order to ensure that the Gelucire® 44/14 and the PEG are not degraded. A temperature of 55° C. corresponds to approximately 10° C. above the point of inflexion of the thermorheogram obtained during the cooling step. In fact, Gelucire® 44/14 exhibits a broad endotherm from 10° C. to 45° C. with an initial melting temperature of approximately 38° C. and a maximum melting temperature of approximately 43° C.

The mixture of Gelucire® 44/14/PEG 6000 in proportions by weight of 65/35 has a dropping point which is determined to be at 58.3° C. The Gelucire® 44/14/PEG 6000 mixture in proportions by weight of 60/40 has a dropping point which is determined to be at 58.6° C.

Cooling the mixture of Gelucire® 44/14 and PEG is preferably carried out by depositing drops of said mixture onto a surface for which the temperature is in the range 4° C. to 8° C.

The invention also concerns a method for the manufacture of a pharmaceutical composition, in which:
  individualized particles of excipient as described above are melted in order to obtain a liquid mass,
  the active principle is introduced into the mass which has been liquefied thereby,
  the mixture obtained is transformed into the desired galenical form.

Independently of the nature of the excipient forming the subject matter of the invention, this series of steps is well known to the person skilled in the art.

Thus, the choice of excipients other than that forming the subject matter of the invention in order to obtain said pharmaceutical composition, as well as the various operations for transformation (tablets, capsules, etc.) are within the purview of the person skilled in the art and do not need to be explained in further detail.

The invention and the advantages thereof will become apparent from the following examples, made with the aid of the accompanying drawings, in which:

FIG. 1 (described above) is an HPLC-CAD (Charged Aerosol Detector) graph which illustrates the distributions of Gelucire® 44/14 alone, PEG 6000 alone, and a mixture (denoted M) of Gelucire® 44/14/PEG 6000 in a weight ratio of 65/35 in accordance with the invention;

FIG. 2 is a photograph of solid pellets in accordance with the invention:

FIG. 3a is a graph illustrating the liberation of piroxicam as a function of time, for a number of formulations:

FIG. 3b is a graph illustrating the liberation of piroxicam as a function of time, for a number of formulations in addition to FIG. 3a:

FIG. 4 is a graph illustrating the liberation of terfenadine as a function of time, for a number of formulations:

FIG. 5 is a graph illustrating the liberation of ibuprofen as a function of time, for a number of formulations.

EXAMPLE 1: PREPARATION OF THE EXCIPIENT IN ACCORDANCE WITH THE INVENTION

Different formulations for solid pellets obtained using the method described above are listed in Table I below.

TABLE I

| Ratio Gelucire ® 44/14/PEG | Temperature of mixture (° C.) | Cooling temperature (° C.) |
|---|---|---|
| Gelucire ® 44/14/PEG 1500 = 10/90 | 48-51 | 5.0-5.5 |
| Gelucire ® 44/14/PEG 4000 = 40/60 | 55-58 | 4.5-6.5 |
| Gelucire ® 44/14/PEG 4000 = 55/45 | 54-55 | 4.8-6.0 |
| Gelucire ® 44/14/PEG 4000 = 60/40 | 51-54 | 4.0-5.0 |
| Gelucire ® 44/14/PEG 4000 = 65/35 | 54-57 | 5.0-6.0 |
| Gelucire ® 44/14/PEG 4000 = 70/30 | 55 | 6.5 |
| Gelucire ® 44/14/PEG 6000 = 60/40 | 57-60 | 5.5 to 8.5 |
| Gelucire ® 44/14/PEG 6000 = 65/35 | 56-57 | 4.5 to 6.5 |
| Gelucire ® 44/14/PEG 6000 = 70/30 | 60 | 5.5 to 7.5 |
| Gelucire ® 44/14/PEG 8000 = 80/20 | 55 | 6.0 |
| Gelucire ® 44/14/PEG 6000 + PEG 1500 = 50/20 + 30 | 53-57 | 5.5-6.5 |
| Gelucire ® 44/14/PEG 6000 + PEG 1500 = 50/30 + 20 | 53-55 | 5.5-7.5 |
| Gelucire ® 44/14/PEG 6000 + PEG 1500 = 65/30 + 5 | 54-59 | 7.2-8.0 |
| Gelucire ® 44/14/PEG 6000 + PEG 4000 = 65/25 + 10 | 55 | 4.0 |
| Gelucire ® 44/14/PEG 6000 + PEG 4000 = 65/30 + 5 | 57-59 | 6.0 |
| Gelucire ® 44/14/PEG 6000 + PEG 8000 = 65/30 + 5 | 51-58 | 4.0-6.2 |

The solid pellets obtained with a mixture of Gelucire® 44/14/PEG 6000 in the following proportions by weight: 65/35, are illustrated in FIG. 2. They were opaque and the flat face was in the form of a disk.

The mixture of Gelucire® 44/14/PEG 6000 in the proportions by weight of 65/35 had a dropping point which was determined to be 58.3° C. The mixture of Gelucire® 44/14/PEG 6000 in the proportions by weight of 60/40 had a dropping point which was determined to be 58.6° C.

EXAMPLE 2: IMPACT OF PEG ON DISSOLUTION OF ACTIVE PRINCIPLES

Example 2.1: Piroxicam

An active principle, piroxicam, was formulated with Gelucire® 44/14. The mixture obtained was cast into a capsule.

The solubility of piroxicam in water at 25° C. is 23 mg/L.

Capsules containing the following formulation were obtained: 20 mg of piroxicam, and 660 mg of Gelucire® 44/14.

The dissolution performance of piroxicam was compared with different formulations of solid pellets obtained in the same manner as described above, the difference being that the Gelucire® 44/14 had previously been prepared in the presence of PEG, as explained above.

The graphs of FIGS. 3a and 3b were obtained, illustrating the liberation L (%) of the active principle as a function of time t in minutes, in which:

FIG. 3a
  the curve B1 (invention) corresponds to a mixture of piroxicam/Gelucire® 44/14/PEG 4000, in which the ratio by weight of Gelucire® 44/14/PEG 4000 is 55/45:
  the curve B2 (invention) corresponds to a mixture of piroxicam/Gelucire® 44/14/PEG 6000, in which the ratio by weight of Gelucire® 44/14/PEG 6000 is 65/35:
  the curve B3 (invention) corresponds to a mixture of piroxicam/Gelucire® 44/14/PEG 4000, in which the ratio by weight of Gelucire® 44/14/PEG 4000 is 60/40:
  the curve B4 (invention) corresponds to a mixture of piroxicam/Gelucire® 44/14/PEG 6000, in which the ratio by weight of Gelucire® 44/14/PEG 6000 is 60/40:
  the curve B5 (invention) corresponds to a mixture of piroxicam/Gelucire® 44/14/PEG 6000, in which the ratio by weight of Gelucire® 44/14/PEG 6000 is 70/30:

the curve B6 (invention) corresponds to a mixture of piroxicam/Gelucire® 44/14/PEG 4000, in which the ratio by weight of Gelucire® 44/14/PEG 4000 is 40/60:
the curve B7 (control 1) corresponds to a mixture of piroxicam/PEG 6000:
the curve B8 (control 2) corresponds to piroxicam alone.
FIG. 3b
the curve B9 (invention) corresponds to a mixture of piroxicam/Gelucire® 44/14/PEG 6000+PEG 1500, in which the ratio by weight of Gelucire® 44/14/PEG 1+PEG 2 is 50/20+30:
the curve B10 (invention) corresponds to a mixture of piroxicam/Gelucire® 44/14/PEG 6000+PEG 4000, in which the ratio by weight of Gelucire® 44/14/PEG 1+PEG 2 is 65/30+5:
the curve B11 (invention) corresponds to a mixture of piroxicam/Gelucire® 44/14/PEG 6000+PEG 8000, in which the ratio by weight of Gelucire® 44/14/PEG 1+PEG 2 is 65/30+5:
the curve B12 (invention) corresponds to a mixture of piroxicam/Gelucire® 44/14/PEG 6000+PEG 4000, in which the ratio by weight of Gelucire® 44/14/PEG 1+PEG 2 is 65/25+10:
the curve B13 (invention) corresponds to a mixture of piroxicam/Gelucire® 44/14/PEG 6000+PEG 1500, in which the ratio by weight of Gelucire® 44/14/PEG 1+PEG 2 is 65/30+5.

It can be seen that all of the mixtures of piroxicam/Gelucire® 44/14/PEG (curves B1 to B6 and B9 to B13) lead to a greater liberation of piroxicam than that of the active principle alone (control 2, curve B8).

The mixtures comprising PEG (curves B1 to B5) resulted in more than 95% liberation after 2 hours, which was highly satisfactory, apart from the mixture of piroxicam/Gelucire® 44/14/PEG 4000, for which the ratio by weight of Gelucire® 44/14/PEG 4000 was 40/60 (curve B6).

The mixtures comprising a combination of two PEGs (curves B9 to B12) resulted in more than 90% liberation after 2 hours, which was satisfactory, apart from the mixture of piroxicam/Gelucire® 44/14/PEG 6000+PEG 1500, for which the ratio by weight of Gelucire® 44/14/PEG 6000+PEG 1500 was 65/30+5 (curve B13).

Furthermore, the performance of the PEG (control 1, curve B7) alone was far poorer than in a mixture with the Gelucire® 44/14.

Example 2.2: Terfenadine

Another active principle, terfenadine, was formulated with Gelucire® 44/14. The mixture was cast into a capsule in a manner that was similar to that of Example 1 above which used piroxicam.

The solubility of terfenadine in water at 25° C. is 250 mg/L.

The dose was 60 mg, for a total of 680 mg of formulation.

The graph of FIG. 4 was therefore obtained, illustrating the liberation L (%) of the active principle as a function of time t in minutes, in which:
the curve C1 (invention) corresponds to a mixture of terfenadine/Gelucire® 44/14/PEG 6000, in which the ratio by weight of Gelucire® 44/14/PEG 6000 is 65/35:
the curve C2 (invention) corresponds to a mixture of terfenadine/Gelucire® 44/14/PEG 6000, in which the ratio by weight of Gelucire® 44/14/PEG 6000 is 60/40;
the curve C3 (control 1) corresponds to a mixture of terfenadine/PEG 6000;
the curve C4 (control 2) corresponds to terfenadine alone.

Here again, it can be seen that the terfenadine/Gelucire® 44/14/PEG mixtures (curves C1 and C2) resulted in approximately 90% liberation after 90 minutes, which was highly satisfactory. This liberation is well above that of the active principle alone, which remained below 10% after 120 minutes (control 2, curve C4).

Furthermore, the performance of PEG alone (control 1, curve C3) was poorer than when mixed with Gelucire® 44/14.

Example 2.3: Ibuprofen

Another active principle, ibuprofen, was formulated with the Gelucire® 44/14/PEG mixtures. The mixture with the active principle was cast into a capsule, in a similar manner to Examples 2.1 and 2.2 above which used piroxicam and terfenadine.

The solubility of ibuprofen in water at 25° C. is 21 mg/L.

The dose was 200 mg, for a total of 680 mg of formulation.

The graph of FIG. 5 was therefore obtained, illustrating the liberation L (%) of the active principle as a function of time t in minutes, in which:
the curve D1 (invention) corresponds to a mixture of ibuprofen/Gelucire® 44/14/PEG 6000, in which the ratio by weight of Gelucire® 44/14/PEG 6000 is 65/35:
the curve D2 (invention) corresponds to a mixture of ibuprofen/Gelucire® 44/14/PEG 6000, in which the ratio by weight of Gelucire® 44/14/PEG 6000 is 60/40;
the curve D3 (control 1) corresponds to a mixture of ibuprofen/PEG 6000;
the curve D4 (control 2) corresponds to the ibuprofen alone.

It can be seen that the mixtures of active principle (ibuprofen)/Gelucire® 44/14/PEG (curves D1 and D2) resulted in approximately 40% liberation after 120 minutes, which was satisfactory and corresponded to a quantity which was 5 times higher than that liberated by the ibuprofen/PEG (control 1, curve D3) mixture or by the ibuprofen alone (control 2, curve D4).

PEG alone (control 1, curve D3) has no impact on the dissolution of the ibuprofen alone (control 2, curve D4) in the dissolving medium.

The invention claimed is:

1. A pharmaceutical or cosmetic excipient composition, said composition consisting of:
   lauroyl macrogolglyceride, and
   polyethylene glycol (PEG),
   wherein said composition is solid at ambient temperature, and is in the form of individualized particles,
   wherein said composition does not comprise a therapeutic active principle,
   wherein the PEG has a molar mass in the range 4000 g/mol to 6000 g/mol,
   wherein the weight ratio of lauroyl macrogolglyceride/polyethylene glycol is in the range 40/60 to 70/30, and
   wherein the individualized particles are in the form of pellets with a dimension which is greater than or equal to 1 mm.

2. The composition according to claim 1, wherein said composition contains at least two PEGs with different molar masses, said molar masses being in the range 4000 g/mol to 6000 g/mol.

3. A method of preparing the composition according to claim 1, said method comprising:

heating lauroyl macrogolglyceride and polyethylene glycol to a temperature T1 in a manner so as to obtain a liquid mixture of lauroyl macrogolglyceride and polyethylene glycol, cooling the mixture of lauroyl macrogolglyceride and polyethylene glycol to a temperature T2 which is lower than the temperature T1, while keeping the mixture liquid, dividing the cooled mixture, and cooling the divided mixture to a temperature T3 which is lower than the temperature T2, thereby obtaining the individualized solid particles.

4. The method according to claim 3, wherein the lauroyl macrogolglyceride and the polyethylene glycol are mixed with each other before the heating step, then the mixture of lauroyl macrogolglyceride and polyethylene glycol is heated to the temperature T1.

5. The method according to claim 3, wherein the temperature T1 is greater than or equal to 80° C.

6. The method according to claim 3, wherein the temperature T2 is greater than or equal to 45° C., and less than or equal to 60° C.

7. The method according to claim 3, wherein said dividing the cooled mixture comprises dividing the cooled mixture into the form of drops and droplets.

8. The method according to claim 3, wherein the temperature T2 is greater than or equal to 55° C., and less than or equal to 60° C.

9. The method according to claim 4, wherein the temperature T1 is greater than or equal to 80° C., and the temperature T2 is greater than or equal to 45° C., and less than or equal to 60° C.

\* \* \* \* \*